United States Patent
Khan et al.

(10) Patent No.: US 12,084,418 B2
(45) Date of Patent: Sep. 10, 2024

(54) SMALL MOLECULE INHIBITORS OF G(ALPHA)I2 PROTEIN AND USES THEREOF

(71) Applicants: Clark Atlanta University, Inc., Atlanta, GA (US); Georgia Tech Research Corporation, Atlanta, GA (US)

(72) Inventors: Shafiq A. Khan, Mableton, GA (US); Silvia Caggia, Decatur, GA (US); Adegboyega K. Oyelere, Marietta, GA (US); Subhasish Tapadar, Atlanta, GA (US)

(73) Assignees: CLARK ATLANTA UNIVERSITY, INC., Atlanta, GA (US); GEORGIA TECH RESEARCH CORPORATION, Atlanta, GA (US)

( * ) Notice: Subject to any disclaimer, the term of this patent is extended or adjusted under 35 U.S.C. 154(b) by 0 days.

(21) Appl. No.: 17/556,820

(22) Filed: Dec. 20, 2021

(65) Prior Publication Data

US 2022/0340526 A1 Oct. 27, 2022

Related U.S. Application Data

(60) Provisional application No. 63/128,744, filed on Dec. 21, 2020.

(51) Int. Cl.
*C07D 209/36* (2006.01)
*C07D 209/08* (2006.01)
*C07D 333/54* (2006.01)

(52) U.S. Cl.
CPC ......... *C07D 209/36* (2013.01); *C07D 209/08* (2013.01); *C07D 333/54* (2013.01)

(58) Field of Classification Search
CPC ............... C07D 209/36; C07D 209/08; C07D 333/54
See application file for complete search history.

(56) References Cited

PUBLICATIONS

Malkov, et al. (abstract) Journal of Organic Chemistry 2009, 74 (16), 5839-5849; Accession No. 2009:727426 retrieved from STN.*
Yoshikai, et al. (abstract) US 20150005494, Jan. 1, 2015; Accession No. 2016:1987749 retrieved from STN.*
Tan, et al. (abstract) Chemical Science (2015), 6(11), 6448-6455; Accession No. 2015:1266246 retrieved from STN.*
Swamy, et al. (abstract) Medicinal Chemistry Research (2015), 24 (9), 3437-3452, Accession No. 2015:1111052, retrieved from STN.*
Luan, et al. (abstract) Bioorganic&Medicinal Chemistry (2013), 21 (7), 1870-1879, Accession No. 2013:245982 retrieved from STN.*
Werkmeister, et al. (abstract) ChemSusChem (2012), 5(4), 777-782, Accesion No. 2012:202115, retrieved from STN.*
Caggia, S. et al., "Novel Role of Giα2 in cell migration: Downstream of PI3-kinase/AKT Rac1 in prostate cancer cells," J. Cell Physiol, 234(1):802-815, (Jan. 2018).
Caggia, S. et al., "Small Molecule Inhibitors Targeting Gαi2 Protein Attenuate Migration of Cancer Cells," Cancers, 12(1631), 15 pgs, (2020).
Doitsides, N. et al., "A Novel Synthesis of Salvadoricine Schiff Bases," Synthetic Communications, 25(9):1411-1418, (1995).
Kumar, D B A. et al., "Synthesis and antimicrobial investigation of some novel phenyl pyrazole, azetidinone and diazenyl ethanone derivatives of benzofurans," Indian Journal of Chemistry, 46B:336-343, (Feb. 2007).
Malkov, A. V. et al., "Asymmetric reduction of imines with trichlorosilane, catalyzed by sigamide, an amino acid-derived formamide: Scope and limitations," The Journal of Organic Chemistry, 74:5839-5849, (2009).
Swamy, P. M. G. et al., "Synthesis, anticancer and molecular docking studies of benzofuran derivatives," Medicinal Chemistry Research, 24:3437-3452, (2015).
Zhong, M. et al., "The Essential Role of Giα2 in Prostate Cancer Cell in Migration," Mol. Cancer Res., 10(10):1380-1388, (Oct. 2012).
WIPO Application No. PCT/US2021/064434, PCT International Search Report and Written Opinion of the International Searching Authority dated Jun. 2, 2022.
Polit, A. et al., "The Gαi protein subclass selectivity to the dopamine $D_2$ receptor is also_decided by their location at the cell membrane," Cell Commun Signal, 18:189, (2020).

* cited by examiner

*Primary Examiner* — Shawquia Jackson
(74) *Attorney, Agent, or Firm* — Alston & Bird LLP

(57) ABSTRACT

The disclosure relates to novel compounds and methods of use of the compounds to maintain the Gα$_i$2 protein in its inactive GDP-bound state. The disclosure describes the knockdown or inhibition of Gα$_i$2 negatively regulated migration of breast and ovarian cancer cell lines. The novel compounds inhibit the migratory behavior of PC3, DU145 and E006AA prostate cancer cell lines. Specifically, the novel compounds block the activation of Gα$_i$2 in oxytocin-stimulated prostate cancer PC3 cells and inhibits the migratory capability of DU145 cells overexpressing constitutively active form of Gα$_i$2, under basal and EGF-stimulated conditions.

6 Claims, 9 Drawing Sheets

Specification includes a Sequence Listing.

CLUSTAL O(1.2.4) multiple sequence alignment

```
GNAI1      MGCTLSAEDKAAVERSKMIDRNLREDGEKAAREVKLLLLGAGESGKSTIVKQMKIIHEAG
GNAI2      MGCTVSAEDKAAAERSKMIDRNLREDGEKAAREVKLLLLGAGESGKSTIVKQMKIIHEDG
           ****:***********:***********************************:****.*

GNAI1      YSEEECKQYRAVVYSNTIQSIIAIIRAMGRLKIDFGDSARADDARQLFVLAGA-AEEGFM
GNAI2      YSEEECRQYRAVVYSNTIQSINAIVKAMGNLQIDFADPSRADDARQLFALSCTAEEQGVL
           ******:*************.**::***.*:***.*.*********.*:.. ***:. :

GNAI1      TAELAGVIKRLWKDSGVQACFNRSREYQLNDSAAYYLNDLDRIAQPNYIPTQQDVLRTRV
GNAI2      PDDLSGVIRRLWADHGVQACFGRSREYQLNDSAAYYLNDLERIAQSDYIPTQQDVLRTRV
            ::*:***:***:*.******.******************:****.:***********

GNAI1      KTTGIVETHFTFKDLHFKMFDVGGQRSERKKWIHCFEGVTAIIFCVALSDYDLVLAEDEE
GNAI2      KTTGIVETHFTFKDLHFKMFDVGGQRSERKKWIHCFEGVTAIIFCVALSAYDLVLAEDEE
           ************************************************:***********

GNAI1      MNRMHESMKLFDSICNNKWFTDTSIILFLNKKDLFEEKIKKSPLTICYPEYAGSNTYEEA
GNAI2      MNRMHESMKLFDSICNNKWFTDTSIILFLNKKDLFEEKITHSPLTICFPEYTGANKYDEA
           ************************************** .***** .***:** :*:**

GNAI1      AAYIQCQFEDLNKRKDTKEIYTHFTCATDTKNVQFVFDAVTDVIIKNNLKDCGLF
GNAI2      ASYIQSKFEDLNKRKDTKEIYTHFTCATDTKNVQFVFDAVTDVIIKNNLKDCGLF
           *:***.:*************************************************
```

FIG. 9

SMALL MOLECULE INHIBITORS OF G(ALPHA)I2 PROTEIN AND USES THEREOF

CROSS REFERENCE TO RELATED APPLICATIONS

This application is a non-provisional application, which claims the benefit of priority to U.S. Provisional Patent Application No. 63/128,744, filed Dec. 21, 2020, which is hereby incorporated by reference in its entirety for all purposes.

STATEMENT REGARDING FEDERALLY SPONSORED RESEARCH OR DEVELOPMENT

Development of the inventions described herein was at least partially funded with government support under grant numbers NIMHD/RCMI G12MD007590 and NIMHD/P20MD002285 awarded by the National Institutes of Health. The U.S. government has certain rights in the invention.

REFERENCE TO A SEQUENCE LISTING SUBMITTED AS A TEXT FILE VIA EFS WEB

The Sequence Listing written in file 572339SEQLIST.txt is 6.29 kilobytes, was created on Dec. 20, 2021, and is hereby incorporated by reference.

FIELD OF THE INVENTION

The present disclosure generally relates to the development of new therapeutic compounds for highly metastatic cancers. Specifically, the disclosure relates to the role heterotrimeric G-protein subunit alpha i2 ($G\alpha_i2$) plays in the inhibition of migratory behavior of cancer cells. Optimized small molecule inhibitors were designed to inhibit activation of the $G\alpha_i2$ subunit.

The disclosure relates to novel compounds which maintain the $G\alpha_i2$ protein in its inactive GDP-bound state. The disclosure describes the knockdown or inhibition of $G\alpha_i2$ negatively regulated migration of breast and ovarian cancer cell lines. The novel compounds inhibit the migratory behavior of PC3, DU145 and E006AA prostate cancer cell lines. Specifically, the novel compounds block the activation of $G\alpha_i2$ in oxytocin-stimulated prostate cancer PC3 cells and inhibit the migratory capability of DU145 cells overexpressing constitutively active form of $G\alpha_i2$, under basal and EGF-stimulated conditions.

BACKGROUND

Metastasis is the leading cause of mortality of patients with cancer. The initiation of metastasis begins with dissemination of tumor cells from the primary tumor to local and distant sites by a process called tumor cell motility.

Tumor cell motility is induced by the activation of several receptors, including receptor tyrosine kinases (RTKs) and G-protein coupled receptors (GPCRs). Activation of GPCRs by chemokines and prostaglandins leads to the activation of a variety of heterotrimeric G proteins. In its inactive state, the heterotrimeric G-protein complex is composed of three subunits $G\alpha$, $G\beta$ and $G\gamma$, with the $G\alpha$ subunit bound to nucleotide GDP. Upon GPCR activation, the receptor undergoes a conformational change, causing the dissociation of $G\alpha$ from the $G\beta$ and $G\gamma$ subunits. GPCR activation results in the $G\alpha$ subunit giving up its GDP in exchange for GTP, thereby freeing the $G\alpha$ subunit to interact with other effector molecules.

Among the $G\alpha$ proteins, there are four major subclasses: $G\alpha_{i/o}$, $G\alpha_s$, $G\alpha_q$ and $G\alpha_{12/13}$. $G\alpha_i$ family members have been implicated in cancer cell migration. Studies have shown that $G\alpha_i3$ is essential for migration in breast cancer cells. $G\alpha_i2$ plays a critical role in oxytocin and EGF signaling to induce cell migration of prostate cancer cells. In addition, studies have established that $G\alpha_i2$ acts at two different levels, both independent and dependent of GPCR signaling, to induce migration and invasion in prostate cancer cells.

Given the high degree of relevance of these proteins during the progression of cancer, the necessity to inhibit the activation of the $G\alpha_i$ proteins is of significant interest. The only commercially available inhibitor for the activation of $G\alpha_{i/o}$ proteins is pertussis toxin (PTX), an enzyme produced by the bacterial pathogen Bordetella pertussis. PTX catalyzes the ADP-ribosylation of the alpha subunits of the heterotrimeric $G_{i/o}$ protein family ($G\alpha_i$, $G\alpha_o$, and $G\alpha_t$; except $G\alpha_z$), preventing the G proteins from interacting with their cognate G protein-coupled receptors (GPCRs). PTX blocks the mitogenic effect of GPCR activated by hormones including epinephrine, lysophosphatidic acid (LPA) and cytokines. In prostate cancer cells, it has been observed that PTX blocked cell migration induced by TGFβ and oxytocin signaling but had no effect on EGF-induced migration. However, as a consequence of PTX's large size, its efficacy is slow, requiring overnight incubation, which leads to compensatory mechanisms.

Further, it has been shown that small molecule inhibitors, targeting $G\alpha_i$ and $G\alpha_q$ subunits, act as guanine nucleotide dissociation inhibitors (GDI). While these molecules are able to partially restore cAMP levels in forskolin-stimulated cells, the molecules are weakly active, showing maximum inhibition of less than 38% at 300 μM.

Thus it would be advantageous to determine the feasibility of small molecule disruption of the function of $G\alpha_i2$ protein as a strategy for mitigating cancer cell migration and to develop novel small molecule anti-metastasis compounds that are potent $G\alpha_i2$ inhibitors. Therefore, there remains a need to understand the essential role of $G\alpha_i2$ protein in mediating tumor cell migration, to assess its potential as a molecular target and to develop novel small molecule anti-metastasis agents as an effective therapy for many metastatic cancers.

SUMMARY

Provided herein are novel $G\alpha_i2$ inhibitor compounds and related methods of use. The compounds are novel small molecule anti-metastasis agents useful in cancer therapy. The compounds produced increased activity in inhibiting intracellular $G\alpha_i2$ activation, resulting in decreased cell migration of multiple cancer cell types.

In one aspect, the Gα$_i$2 inhibitor compound comprises the compound of Formula I,

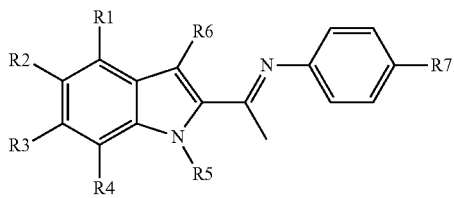

Formula I wherein R1, R2 and R3 include H, OH and halogens such as Cl, Br and I; R4 is H, alkyl, halo-alkyl and aryl, wherein the alkyl, halo-alkyl and aryl are preferably methyl, ethyl, trifluoromethyl, phenyl and pyridyl groups, wherein the phenyl and pyridyl groups are optionally substituted at the ortho, meta and para positions; R5 is H, methyl, and ethyl; R6 is H, OH and halogens such as Cl, Br and I; and R7 is OH and OMe.

In a second aspect, the Gα$_i$2 inhibitor compound comprises the compound of Formula II,

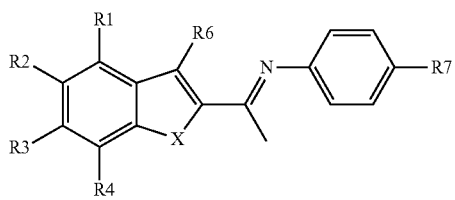

Formula II wherein R1, R2 and R3 include H, OH and halogens such as Cl, Br and I; R4 is H, alkyl, halo-alkyl and aryl, wherein the alkyl, halo-alkyl and aryl are preferably methyl, ethyl, trifluoromethyl, phenyl and pyridyl groups, wherein the phenyl and pyridyl groups are optionally substituted at the ortho, meta and para positions; R5 is H, methyl, and ethyl; R6 is H and halogens such as Cl, Br and I; R7 is OH and OMe; and X is S and O.

In one embodiment, the Gα$_i$2 inhibitor compound comprises the compound of Compound 14.

Compound 14

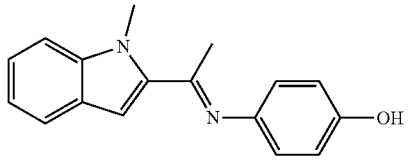

In another embodiment, the Gα$_i$2 inhibitor compound comprises the compound of Compound 9b.

Compound 9b

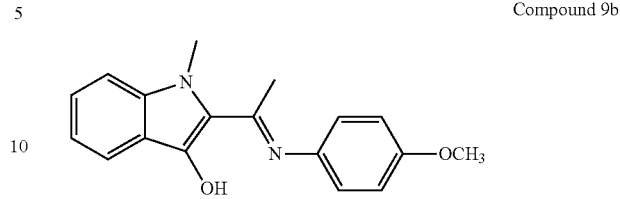

In yet another embodiment, the Gα$_i$2 inhibitor compound comprises the compound of Compound 9a.

Compound 9a

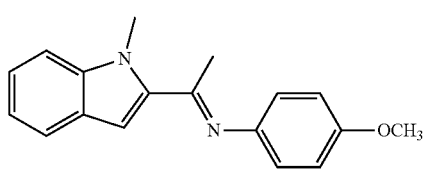

In another embodiment, the Gα$_i$2 inhibitor compound comprises the compound of Compound 13.

Compound 13

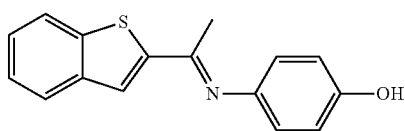

Compounds of Formula (I) and (II) are useful as Gα$_i$2 inhibitor compounds to prohibit migration of cancer cells. In a third aspect, the invention is a method of using a compound of Formula (I) and (II) to inhibit cell migration in prostate cancer, breast cancer and ovarian cancer.

Additional advantages will be set forth, in part in the description which follows, in part will become obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below. Like numbers represent the same elements throughout the figures. The drawing figures are not necessarily to scale and certain features may be shown exaggerated in scale or in a somewhat generalized or schematic form in the interest of clarity and conciseness. For more complete understanding of the features and advantages of the present invention, reference is now made to the detailed description of the invention along with the accompanying figures, wherein:

FIG. 1B panel ii illustrates an overlay of docked orientations of compound 12 in the presence (shown in cyan) or absence (shown in yellow) of $Mg^{2+}$ ion, and provides evidence of the productive interaction between the phenolic moiety of compound 12 and the active site $Mg^{2+}$ ion.

FIG. 1C panel ii depicts an overlay of docked orientations of compound 12 (shown in cyan) and compound 9b (shown in grey); the overlay of the compounds is depicted to demonstrate that the methyl ether group constitutes a hindrance to the productive interaction with the active site $Mg^{2+}$ ion.

FIG. 1D panel ii depicts the overlay of the docked outputs of compound 12 (shown in cyan), compound 13 (shown in orange) and compound 14 (shown in brown) revealing that the benzothiophene ring of compound 13 and the benzopyrrole ring of compound 14 adopt orientations where their sulfur and N-methyl amino groups (respectively) are placed in the hydrophobic pocket occupied by the thiophene-hydoxyl group of compound 12.

FIG. 9 depicts a multiple sequence alignment showing $G\alpha_i1$ (SEQ ID NO: 1) and $G\alpha_i2$ (SEQ ID NO: 2) proteins having more than 90% amino acid sequence similarities and their GTP-binding sites conserved.

DETAILED DESCRIPTION

Heterotrimeric G-proteins are ubiquitously expressed in many cancers. These proteins transduce signals from activated G-protein coupled receptors, have numerous biological functions, and as a result, have significant potential as target molecules in cancer therapy. The development of treatments that inhibit cell motility or inhibit proteins involved in the enhancement of cell migration represent an interesting and attractive approach for controlling metastatic dissemination.

Tumor cell motility, or cell migration, is a complex network of signaling events that are induced by the activation of multiple receptors, including receptor tyrosine kinases (RTKs) and G protein-coupled receptors (GPCRs). In particular, multiple GPCRs are involved during metastatic events in numerous cancers and they are considered potential targets to develop new therapeutic approaches. However, very few compounds that inhibit cell migration have been developed and tested in clinical trials.

Appleton et al. identified small molecule GDI inhibitors which weakly inhibit $G\alpha_i$ subunits at high micromolar concentrations while maintaining intact the stimulation of the $G\beta\gamma$ signaling. The most tractable of these weak $G\alpha_i$ inhibitors, compound 12 (shown in FIG. 2), was studied using molecular docking with the crystal structure $G\alpha_i1$-GDP (PDB: 2OM2) to understand the interaction of compound 12 with $G\alpha_i1$. New compounds were then designed and synthesized to enhance the binding affinity to the $G\alpha_i2$ subunit.

Subsequently, the synthesized compounds were screened for their effects on intracellular $G\alpha_i2$ activity and on cell migration in multiple cancer cell types. The new compounds were found to be particularly potent in inhibiting cell migration and preventing $G\alpha_i2$ activation. The data confirmed the essential role of $G\alpha_i2$ protein in mediating tumor cell migration and confirmed its viability as a molecular target for developing novel small molecule anti-metastasis agents in cancer therapy.

Figures 3A, 3B, 3C:
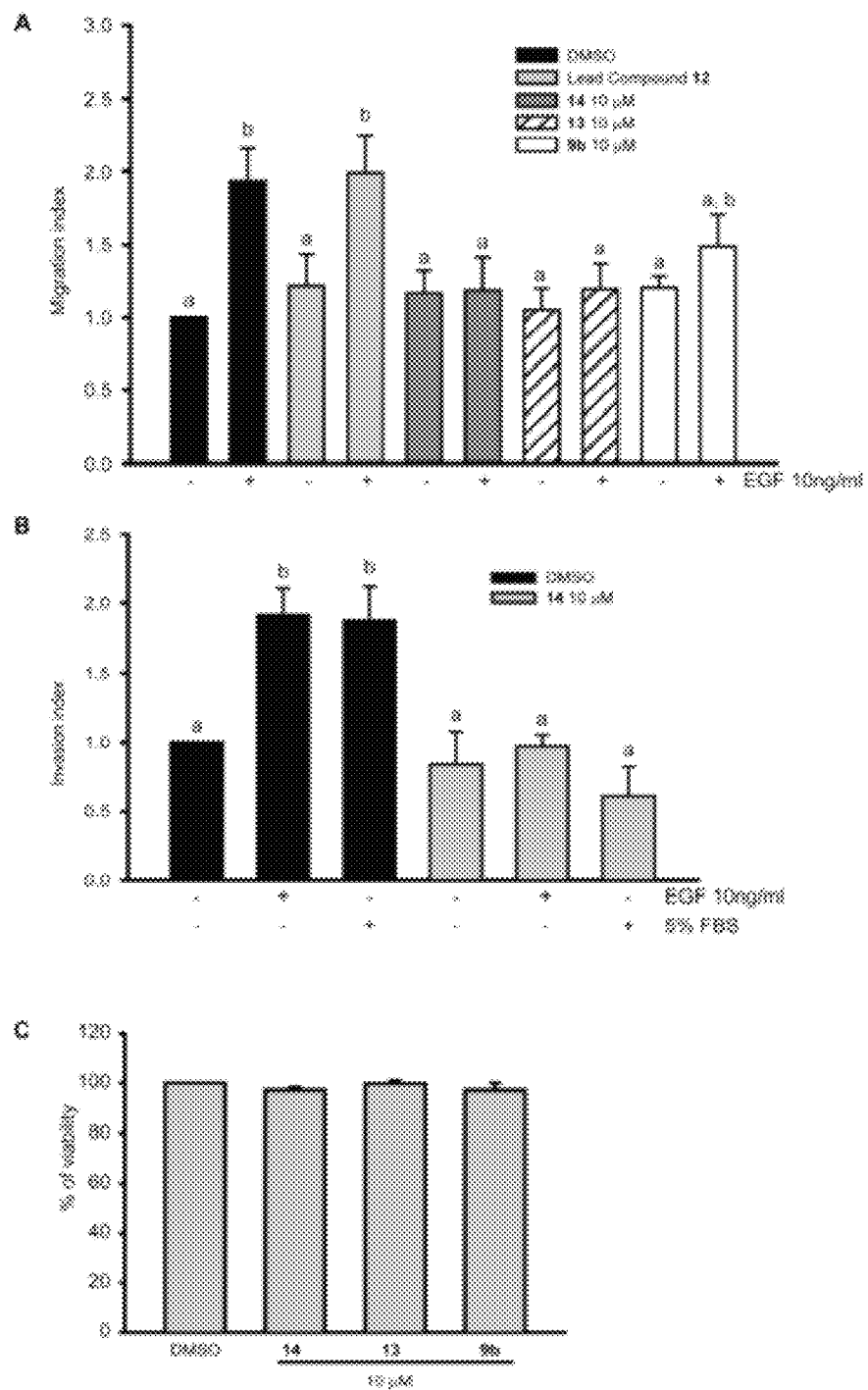
FIG. 3A is a bar graph depicting a migration assay of PC3 cells incubated with and without compounds 12, 9b, 13 and 14 (at final concentrations of 10 μM) and subjected to transwell migration assays in the presence of EGF (10 ng/ml). The results are expressed as migration index defined as average number of cells per field for the ligand tested/the average number of cells per field for the vehicle control. Each bar represents mean±SEM (n=3) and analyzed by ANOVA and Duncan's modified range tests. Different letters represent significant differences (P<0.05) among various treatment groups.
FIG. 3B is a bar graph depicting an invasion assay of PC3 cells treated with or without compound 14 at a final concentration of 10 μM in response to EGF (10 ng/ml). Results are expressed as invasion index defined as average number of cells per field for the ligand tested/the average number of cells per field for the vehicle control. Each bar represents mean f SEM (n=3). Significant differences (P<0.05) among different groups are represented with different lowercase letters. 5% FBS was used as a positive control.
FIG. 3C is a graph depicting a viability study of PC3 cells treated for 24 hours with inhibitor compounds 9b, 13 and 14, at 10 μM. MTS assays were conducted for 4 hours and the results were expressed as % of viable treated cells against the control cells. Each bar represents mean±SEM (n=3).

Compounds 9a, 9b, 13 and 14 were screened against several cancer cell types. These compounds impaired activation of $G\alpha_i2$ by inhibiting conversion of the $G\alpha_i2$ subunit from GDP- to GTP-state. Compounds 13 and 14, at concentration of 10 μM, significantly reduced the migratory capability of PC3 cells stimulated with EGF (FIG. 3A). Further, the invasive capabilities of PC3 cells were inhibited by compound 14 (FIG. 3B).

Figures 4A, 4B:
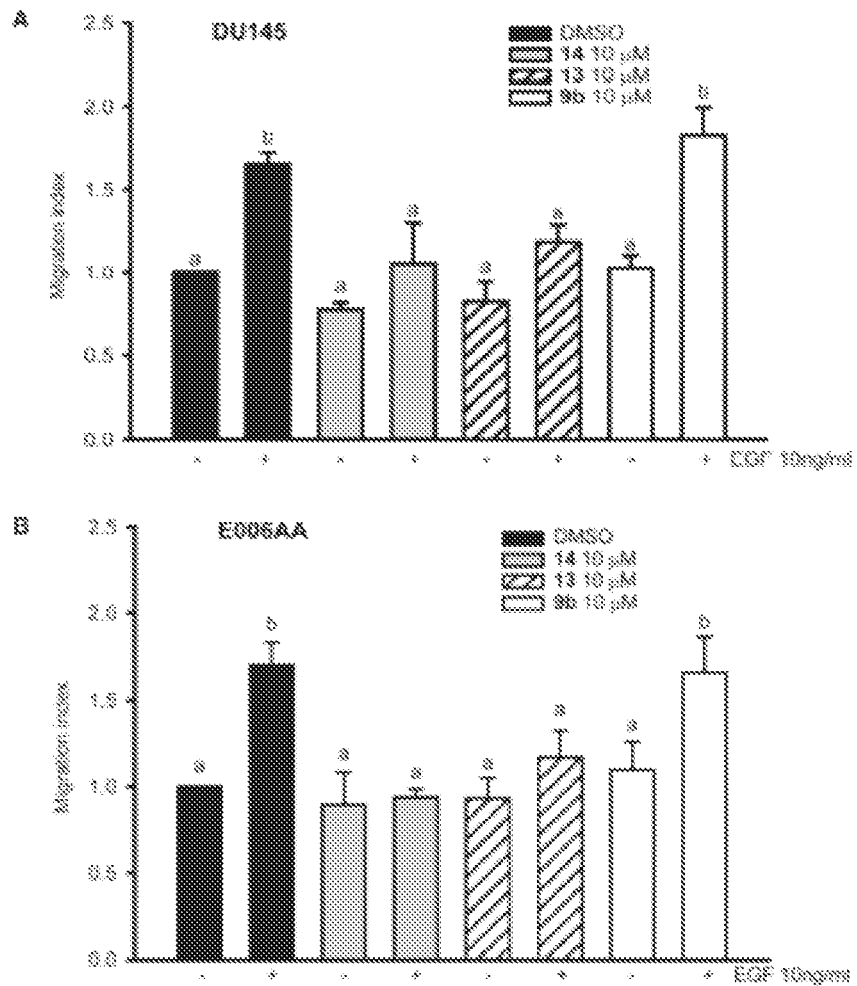
FIG. 4A is a graph depicting a migration assay in DU145 cells in the response to EGF using compounds 9b, 13 and 14 each at concentrations of 10 μM.
FIG. 4B is a graph depicting a migratory assay in E006AA cells in the response to EGF using compounds 9b, 13 and 14 each at concentrations of 10 μM.

It was also observed that compounds 13 and 14 (at 10 μM) reduced the EGF-induced migration in DU145 and E006AA cells (FIG. 4). The enhanced cell migration inhibition displayed by compounds 13 and 14 confirmed results from docking studies (FIG. 1). These results confirm that the new small molecule inhibitors significantly reduce migration and invasion in several prostate cancer models.

Figures 5A, 5B:
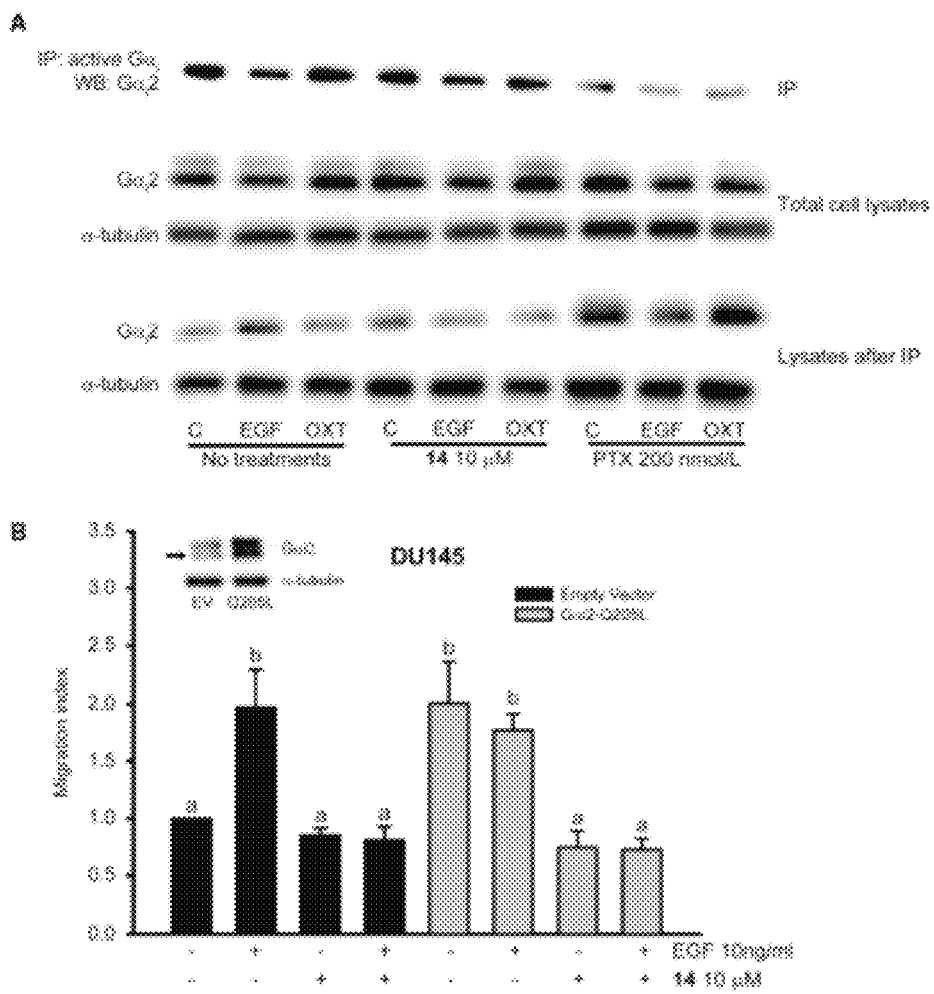
FIG. 5A depicts Western blot analysis demonstrating reduced activation of $G\alpha_i2$ with compound 14 in PC3 cells. Total cell lysates from different treatments were immunoprecipitated using anti-active $G\alpha_i$ antibody, and the immunoprecipitates were resolved on an SDS-PAGE and immunoblotted with anti-$G\alpha_i2$ antibody.
FIG. 5B is a graph depicting results of cell migrations in DU145 overexpressing the Empty Vector (DU145-EV) and DU145 overexpressing constitutively active form of $G\alpha_i2$ (DU145-$G\alpha_i$2-Q205L) cells performed after incubation with compound 14 at 10 μM, in response to EGF (10 ng/ml). Results are expressed as migration index. Each bar represents mean±SEM (n=3). Significant differences (P<0.05) among different groups are represented with different lowercase letters.

To investigate whether the novel compounds specifically inhibited the activation of $G\alpha_i2$ protein, PC3 cells were incubated with compound 14 (at 10 μM). After immunoprecipitation with anti-active $G\alpha_i$ antibody, Western blot analysis using a specific anti-$G\alpha_i2$ antibody showed that in the presence of compound 14, the levels of active $G\alpha_i2$ were reduced after stimulation with OXT, compared to controls (FIG. 5A).

In the second set of experiments, constitutively active form of $G\alpha_i2$ was overexpressed in DU145 cells. Compound 14 significantly reduced migration in DU145-$G\alpha_i2$-Q205L cells expressing constitutively active form of $G\alpha_i2$ (FIG. 5B). Thus, compound 14 inhibited the activation of $G\alpha_i2$, effectively competing with GTP at its binding site.

Using a genetic approach to achieve knockdown of $G\alpha_i2$, it was also observed that the protein is required for migration in other cancer cell types, including MCF7 breast cancer cells and SKOV3 ovarian cancer cells. Importantly, compound 14 significantly reduced migration of both cell lines.

In conclusion, we disclose new small molecules which target $G\alpha_i2$, resulting in increased inhibition of the migration of several cancer cell types, and the methods of using the same. The synthesized compounds were shown to be effective at reducing motility of prostate, breast and ovarian cancer cell lines.

EXPERIMENTAL

Materials and Methods
Chemicals and Reagents

Anhydrous solvents and other reagents were purchased either from Sigma-Aldrich (St. Louis, MO) or VWR International (Radnor, PA) and were used without further purification. Analtech silica gel plates (60 F254) were utilized for analytical TLC, and Analtech preparative TLC plates (UV254, 2000 μm) were used for purification. Silica gel (200-400 mesh) was used in column chromatography. TLC plates were visualized using UV light, anisaldehyde, and/or iodine stains. NMR spectra were obtained on a Varian-Gemini 400 MHz and Bruker Ascend™ 500 and 700 MHz magnetic resonance spectrometer. $^1$H NMR spectra were recorded in parts per million (ppm) relative to the residual peaks of CHCl$_3$ (7.24 ppm) in CDCl$_3$ or CHD$_2$OD (4.78 ppm) in CD$_3$OD or DMSO-d$_5$ (2.49 ppm) in DMSO-d$_6$. MestReNova (version 11.0) was used to process the original "fid" files. High-resolution mass spectra were gathered with the assistance of the Georgia Institute of Technology mass spectrometry facility (Atlanta, GA).

Reaction Schemes

FIG. S1

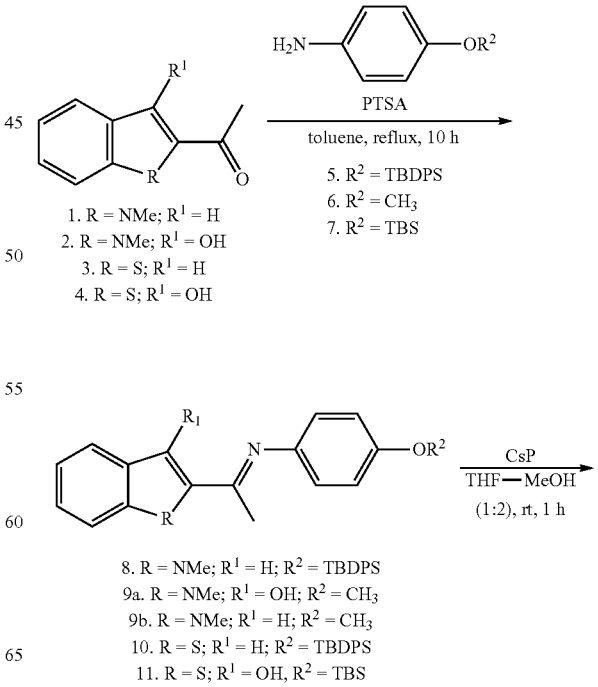

-continued

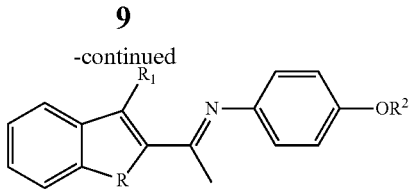

12. R = S; R¹ = OH; R² = H
13. R = S; R¹ = R² = H
14. R = NMe; R¹ = R² = H

Synthesis of ketimines 9a-b, 12-14

General Procedure for Preparation of Ketimines (Method A). A solution of the corresponding methylketones 1-4 (1 mmol), corresponding amines 5-7 (1.2 mmol) and p-toluenesulfonic acid monohydrate (5 mol %) in anhydrous toluene (5 mL) was heated under reflux with a Dean-Stark trap for 10 hour, then cooled and neutralized by adding saturated aqueous NaHCO$_3$ solution; The organic layer was then separated. The aqueous layer was further extracted with ethyl acetate (20 mL) and the combined organic layers were washed with water (10 mL), brine (10 mL), dried over anhydrous Na$_2$SO$_4$, and then filtered and evaporated to dryness. The residue was purified by preparative chromatography with a hexane-ethyl acetate mixture as mobile phase to produce the ketimine compounds 8-11.

General Procedure for silyl deprotection (Method B). Silyl protected ketimine compounds 8, 10, and 11 were dissolved in 2:1 MeOH-THF, CsF (2 equiv.) was added to the solution and the resultant solution was stirred for 1 h. The reaction was quenched by adding water and extracted with ethyl acetate (20 mL) and the aqueous layer was separated. Ethyl acetate layer was washed with brine (10 mL), dried over anhydrous Na$_2$SO$_4$, filtered, and concentrated to dryness. The residue was purified by preparative chromatography with a hexane-ethyl acetate mixture as mobile phase to produce the target molecules 12-14.

(E)-N-(4-((tert-butyldiphenylsilyl)oxy)phenyl)-1-(1-methyl1H-indol-2-yl)ethan-1-imine (Compound 8) using Method A, was purified by preparative chromatography using 5% ethyl acetate-hexane mixture as mobile phase. Yellow oil; yield: 15%. $^1$H NMR (400 MHz, CDCl$_3$) δ 7.75-7.66 (m, 4H), 7.64-7.55 (m, 1H), 7.45-7.31 (m, 6H), 7.28 (t, J=7.6 Hz, 1H), 7.23-7.18 (m, 1H), 7.13-7.05 (m, 1H), 6.97 (s, 1H), 6.78-6.69 (m, 2H), 6.57 (d, J=8.3 Hz, 2H), 4.14-4.00 (s, 3H), 2.23 (s, 3H), 1.09 (s, 9H).

(E)-2-(1-((4-methoxyphenyl)imino)ethyl)-1-methyl-1H-indol-3-ol (Compound 9a), using Method A, was purified by preparative chromatography using 40% ethyl acetate-hexane mixture as mobile phase. Orange solid; yield: 15%. $^1$H NMR (700 MHz, CDCl$_3$) δ 7.81 (d, J=7.7 Hz, 1H), 7.40 (t, J=7.6 Hz, 1H), 7.09 (dd, J=13.1, 8.2 Hz, 3H), 6.94 (t, J=7.3 Hz, 1H), 6.89 (d, J=8.4 Hz, 2H), 3.80 (s, 3H), 3.49 (s, 3H), 2.40 (s, 3H). $^{13}$C NMR (176 MHz, CDCl$_3$) δ 177.58, 157.76, 150.15, 149.89, 131.60, 131.45, 126.43, 123.41, 123.17, 121.53, 118.80, 114.70, 114.66, 110.93, 55.72, 35.93, 17.07. HRMS (EI) m/z Calcd. for C$_{18}$H$_{18}$O$_2$N$_2$ [M]+: 294.1371, found 294.1368.

(E)-N-(4-methoxyphenyl)-1-(1-methyl-1H indole-2-yl)ethane-1-imine (Compound 9b), using Method A, was purified by preparative chromatography using 10% ethyl acetate-hexane mixture as mobile phase. Yellow solid; yield: 30%. $^1$H NMR (400 MHz, CDCl$_3$) δ 7.64 (dq, J=4 7.9, 0.8 Hz, 1H), 7.37 (dq, J=8.4, 0.9 Hz, 1H), 7.30 (ddd, J=8.2, 6.9, 1.1 Hz, 1H), 7.11 (ddt, J=7.7, 6.9, 0.9 Hz, 1H), 7.00 (d, J=0.8 Hz, 1H), 6.96-6.85 (m, 2H), 6.82-6.69 (m, 2H), 4.15 (s, 3H), 3.81 (s, 3H), 2.30 (s, 3H). $^{13}$C NMR (176 MHz, CDCl$_3$) δ 160.4, 156.2, 144.4, 140.3, 137.8, 135.1, 126.6, 125.4, 124.1, 121.7, 120.2, 114.70, 111.3, 110.2, 107.5 55.7, 33.1, 18.8. HRMS (EI) m/z Calcd. for C$_{18}$H$_{19}$ON$_2$ [M+H]+: 279.1492, found 279.1493.

(E)-1-(benzo[b]thiophen-2-yl)-N-(4-((tert-butyldiphenylsilyl)oxy)phenyl)ethan-1-imine (Compound 10), using Method A, was purified by preparative chromatography using 10% ethyl acetate-hexane mixture as mobile phase. Yellow solid; yield: 28%. $^1$H NMR (400 MHz, CDCl$_3$) δ 7.82-7.74 (m, 2H), 7.74-7.68 (m, 4H), 7.63 (d, J=0.9 Hz, 1H), 7.44-7.38 (m, 2H), 7.38-7.29 (m, 6H), 6.77-6.72 (m, 2H), 6.61-6.56 (m, 2H), 2.26 (s, 3H), 1.09 (s, 9H).

(E)-2-(1-(4-((tert-butyldiphenylsilyl)oxy)phenyl)imino) ethyl)benzo[b]thiophene-3-ol (Compound 11), using Method A, was purified by preparative chromatography using 10% ethyl acetate-hexane mixture as mobile phase. Yellow solid; yield: 6%. $^1$H NMR (700 MHz, CDCl$_3$) δ 7.96 (dd, J=7.9, 3.3 Hz, 1H), 7.57 (dd, J=7.9, 2.8 Hz, 1H), 7.52 (t, J=7.6 Hz, 1H), 7.48-7.43 (m, 1H), 7.40 (q, J=8.1, 5.5 Hz, 1H), 7.30-7.26 (m, 1H), 7.07-7.02 (m, 2H), 6.86-6.82 (m, 2H), 2.36-2.20 (m, 3H), 1.03-0.91 (m, 8H), 0.28-0.12 (m, 5H).

(E)-2-(1-((4-hydroxyphenyl)imino)ethyl)benzo[b]thiophen-3-ol (Compound 12), using. Method B, was purified by preparative chromatography using 40% ethyl acetate-hexane mixture as mobile phase. Yellow solid; yield: 84%. $^1$H NMR (700 MHz, MeOH-d$_4$) δ 7.83 (d, J=7.8 Hz, 1H), 7.60 (dd, J=8.0, 2.8 Hz, 1H), 7.45 (t, J=7.6 Hz, 1H), 7.25 (t, J=7.0 Hz, 1H), 7.12-7.04 (m, 2H), 6.80 (t, J=5.3 Hz, 2H), 2.29 (d, J=2.9 Hz, 3H). $^3$C NMR (176 MHz, CDCl$_3$) δ 182.17, 161.85, 159.57, 154.99, 142.34, 134.80, 131.31, 130.04, 127.03, 125.36, 5 124.28, 123.59, 116.49, 56.21, 19.48, 14.35. HRMS (ESI) m/z Calcd. for C$_{16}$H$_{14}$O$_2$NS [M+H]+: 284.0740, found 284.0738.

(E)-4-((1-(benzo[b]thiophen-2-yl)ethylidene)amino)phenol (Compound 13), using Method B, was purified by preparative chromatography using 30% ethyl acetate-hexane mixture as mobile phase. Yellow solid; yield: 65%. $^1$H NMR (700 MHz, CDCl$_3$) δ 7.79 (dd, J=23.2, 7.7 Hz, 2H), 7.65 (s, 1H), 7.34 (dt, J=18.0, 7.3 Hz, 2H), 6.93 (d, J=8.0 Hz, 2H), 6.72 (d, J=8.0 Hz, 2H), 2.32 (s, 3H). $^{13}$C NMR (176 MHz, CDCl$_3$) δ 160.91, 153.26, 146.99, 142.83, 141.22, 139.81, 125.95, 125.29, 124.57, 124.43, 122.58, 121.59, 115.82, 63.24, 52.91, 17.15, 8.05. HRMS (ESI) m/z Calcd. for C$_{16}$H$_{14}$ONS [M+H]+: 268.0791, found 268.0790.

(E)-4-((1-(1-methyl-1H-indol-2-yl)ethylidene)amino) phenol (Compound 14), using Method B, was purified by preparative chromatography using 20% ethyl acetate-hexane mixture as mobile phase. Brown solid; yield: 53%. $^1$H NMR (700 MHz, CDCl$_3$) δ 7.64 (d, J=7.9 Hz, 1H), 7.37 (d, J=8.3 Hz, 1H), 7.29 (t, J=7.7 Hz, 1H), 7.11 (t, J=7.4 Hz, 1H), 7.00 (s, 1H), 6.83 (d, J=8.1 Hz, 2H), 6.70 (d, J=8.1 Hz, 2H), 4.14 (s, 3H), 2.29 (s, 3H). $^{13}$C NMR (176 MHz, CDCl$_3$) δ 160.58, 151.93, 144.53, 140.15, 137.82, 126.60, 124.11, 121.74, 121.17, 120.20, 115.90, 110.22, 107.56, 33.16, 18.85. HRMS (ESI) m/z Calcd. for C$_{17}$H$_{17}$ON$_2$ [M+H]+: 265.1330, found 265.1335.

FIG. S1 depicts the reaction routes for the synthesis of compounds 9a, 9b, 12, 13 and 14.

Anti-α-tubulin and bovine serum albumin (BSA) were obtained from Sigma-Aldrich (St. Louis, MO). Rat tail collagen, Matrigel and transwell inserts were obtained from BD Biosciences (San Jose, CA). DAPI (4', 6-Diamidino-2-Phenylindole, Dilactate) was purchased from Invitrogen by Thermo Fisher Scientific (Eugene, OR). Rabbit polyclonal anti-Gα$_i$2 antibody (sc-7276), control and Gα$_i$2 siRNAs, and transfection reagents (sc-295228) were purchased from Santa Cruz Biotechnology (Dallas, TX). Epidermal growth factor (EGF) was obtained from Life Technologies (Grand Island, NY). The anti-active $G\alpha_i$ antibody was purchased from NewEast Biosciences (Malvern, PA). The anti-rabbit and anti-mouse immunoglobulins coupled with horseradish peroxidase (IgG-HRP), were obtained from Promega (Madison, WI). Cell culture reagents were obtained from Mediatech, Inc. (Manassas, VA). The pcDNA3.1 control vector or vector encoding the constitutively active form of $G\alpha_i2$ (pcDNA3.1-EV and pcDNA3.1-$G\alpha_i$2-Q205L, respectively) were purchased from cDNA Resource Center (Bloomsberg, PA).

Cell Lines and Cell Culture

Human prostate cancer cell lines (DU145 and PC3) were obtained from American Type Culture Collection (ATCC) (Rockville, MD). DU145 and PC3 are androgen independent cell lines, derived from brain and bone metastatic sites, respectively. They were maintained in Minimum Essential Medium, supplemented with 5% FBS, in a 5% $CO_2$ environment at 37° C. E006AA cells are derived from localized prostate cancer in a patient of African American descent. These cells were maintained in Dulbecco's Modified Eagle Medium, supplemented with 5% FBS, in a 5% $CO_2$ environment at 37° C.

Human breast adenocarcinoma cell line MCF7 and human ovarian adenocarcinoma cell line SKOV3 were obtained from American Type Culture Collection (ATCC) (Rockville, MD) and maintained in Dulbecco's Modified Eagle Medium, supplemented with 5% FBS, in a 5% $CO_2$ environment at 37° C.

Small Molecule Preparation and Docking

Molecular docking was performed on crystal structure of $G\alpha_i1$-GDP bound to the Goloco Motif of Rgs14 (PDB: 2OM2) using Autodock Vina run through PyRx to manage the workflow and PyMol to visualize the results. Prior to docking, the water molecules and RGS14 protein motif were removed. Ligands were prepared by generating an energy minimized 3D structure in ChemBioDraw3D (Ultra 13.0). This was followed by processing with Autodock Tools 1.5.4. Docking runs were performed within a 25-30 Å cubic search space surrounding the binding pocket in the presence and absence of active site $Mg^{2+}$ ion through PyRx. To ensure the results were comparable, the selected docking results are models with highest binding affinity and similar orientation as compound 12.

For biological assays, the compounds were dissolved in DMSO at a starting concentration of 0.05 mM (compound 12) and 0.1 mM (compounds 9a-b, 13 and 14) and then diluted in culture media to the final concentrations used for the assays.

Immunoprecipitation of Active $G\alpha_i$

PC3 cells ($3\times10^6$ cell/dish) were incubated with or without inhibitor compound 14 (10 µM) for 30 minutes and then treated with EGF (10 ng/ml) or oxytocin (200 nmol/L) for additional 30 minutes. Cells were lysed in ice-cold cell lysis buffer (Cell Signaling Technology) and snap-frozen in liquid nitrogen. Total cell lysates, containing approximately 1000 µg of proteins, were used for immunoprecipitation. The lysates were incubated with 1 µg of anti-active $G\alpha_i$ antibody, overnight at 4° C. Immunocomplexes were collected by centrifugation after incubation with protein A/G-Sepharose beads for 48 h (Santa Cruz Biotechnology) and were analyzed by Western blot analysis with specific anti-$G\alpha_i$2 antibody (Abcam).

Transient Transfection with Constitutively Active $G\alpha_i$2-Q205L Plasmid

DU145 cells were seeded in 6-well plates at a density of $2.0\times10^5$ cells per well and transfected with pcDNA3.1-EV and pcDNA3.1-$G\alpha_i$2-Q205L, using ViaFect™ transfection reagent, according to the manufacturer's protocol. Briefly, media with no antibiotics (200 µl/well) containing 2 µg of plasmids DNA were mixed with the transfection reagent (6 µl/well) and, after 20 minutes, the mixtures were added drop by drop on the cells and the cells were cultured for 48 hours. Then the cells were harvested and used for several assays.

Western Blot Analysis

Western blot analyses were performed. Briefly, protein samples (30-35 µg proteins) were separated on 10% SDS-PAGE gels and transferred to polyvinylidene difluoride (PVDF) membranes (Millipore Corp., Bedford, Massachusetts). After blocking, the membranes were incubated with several primary antibodies, at appropriate dilutions (1:500 for Giα2; 1:3000 for α-tubulin) overnight at 4° C. After washing, the blots were incubated with appropriate secondary antibodies and developed in ECL mixture, using Syngene PXi Imaging System, according to the manufacture's manual. α-tubulin was used as loading control.

Cell Viability Assay

Cell viability assays were performed using CellTiter 96® AQueous One Solution Cell Proliferation Assay (MTS) from Promega, according to the manufacture's protocol. Briefly, $5.0\times10^4$ cells/well were plated in a 96 well plates and incubated in a 5% $CO_2$ environment at 37° C. overnight. After 24 hours the medium was replaced with fresh medium, containing several compounds at the appropriate concentrations. Diluted DMSO was used as a control. MTS assays were performed after 24 hours and the absorbance read at 490 nm, using a spectrophotometer.

Cell Migration and Invasion Assays

In vitro cell migration and invasion assays were conducted using 24-well transwell inserts (8 µm). The transwell inserts were coated with 50 mg/ml of rat tail collagen for migration assays, and with 50 µl of a 1:4 Matrigel/Coating buffer solution for invasion assays. Cells were suspended at the appropriate density in appropriate media and treated with the inhibitors, at specific concentrations. For migration assays, EGF was used as a chemoattractant (10 ng/ml) for PC3, DU145, E006AA and SKOV3 cells; 10% FBS was used for MCF7 cells. The plates were incubated at 37° C. for 5 hours (DU145, PC3 and SKOV3), 24 hours (E006AA) or 48 hours (MCF7) for migration assays, and 48 hours for invasion assays. After fixation, the cells were stained with 3 ng/ml of DAPI and images of five non-overlapping fields were captured using Axiovert 200M, Carl Zeiss (Thornwood, NY) microscope. The number of stained nuclei were determined with automatic counting using image analysis software (ZEN 2012; Carl Zeiss). Results were expressed as migration or invasion index defined as: the average number of cells per field for test substance/the average number of cells per field for the medium control.

Sequence Alignment

According to Clustal 0 (1.2.4) (https://www.ebi.ac.uk/Tools/msa/clustalo/) multiple sequence alignment, $G\alpha_i1$ and $G\alpha_i2$ proteins have more than 90% amino acid sequence similarities and their GTP-binding sites are conserved (FIG. S3).

Statistical Analysis

All experiments were repeated at least three times using different cell preparations. The results are presented as mean±SEM of three independent experiments and images from a single representative experiment are presented.

ANOVA and Duncan's modified multiple range tests were employed to assess the significance of differences among various treatment groups (p<0.05).

Results

Gα$_i$2 Inhibitors Design: Molecular Docking Analysis and Synthesis

Figures 1A, 1B, 1C, 1D:
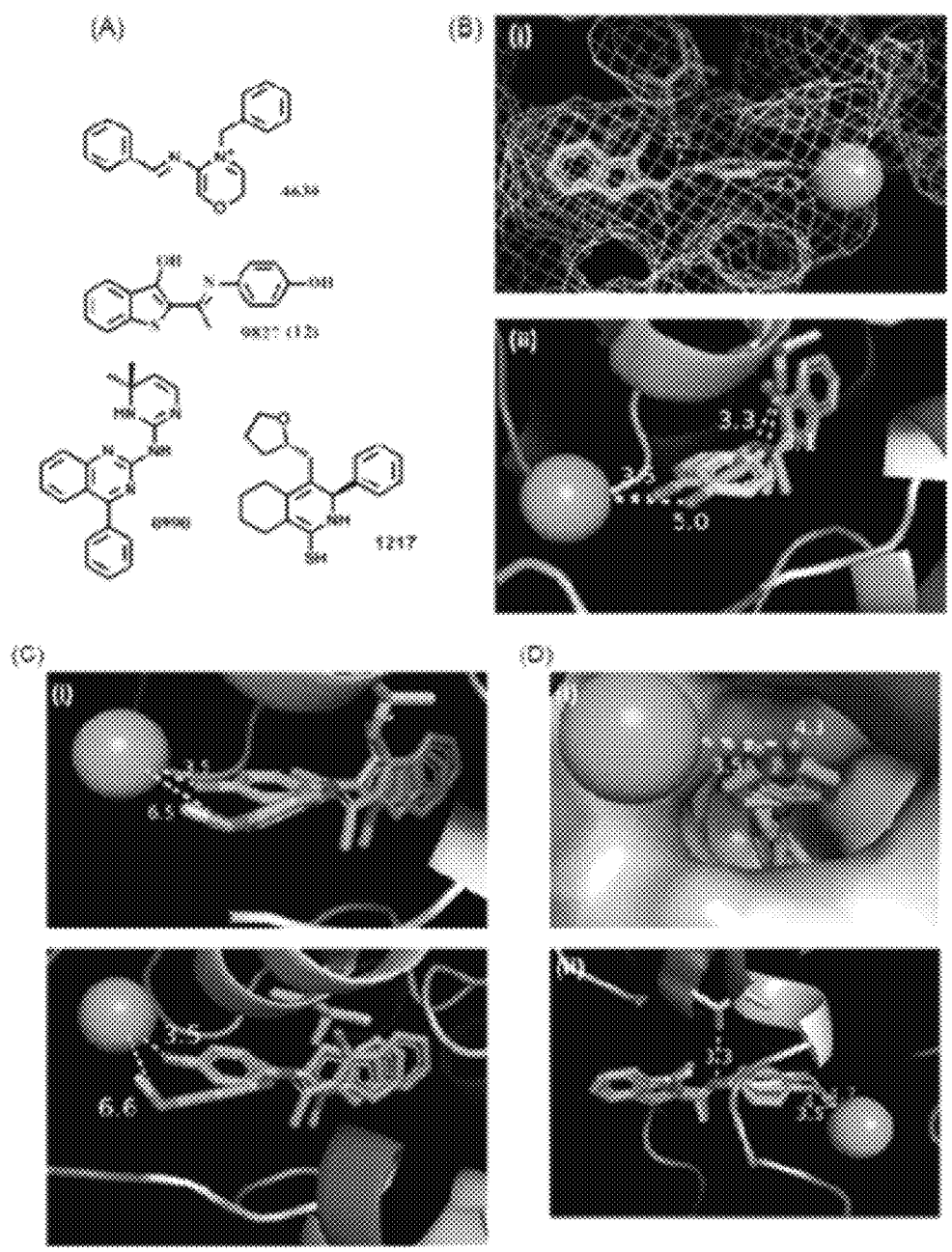
FIG. 1A discloses the structure of four Gα$_i$1 selective inhibitors, including ketamine 9827 (compound 12).
FIG. 1B panel i illustrates the docked output of compound 12 at the active site of Gα$_i$1-GDP, showing the placement of the thiophene-hydroxyl and benzothiophene sulfur groups.
FIG. 1C panel i depicts the docked orientations of compound 12 (shown in cyan) and compound 9a (shown in teal); the overlay of the compounds is depicted to demonstrate that the methyl ether group constitutes a hindrance to the productive interaction with the active site $Mg^{2+}$ ion.
FIG. 1D panel i depicts an overlay of the docked outputs of compound 12 (shown in cyan) and compound 13 (shown in orange) revealing that their phenolic moieties occupy nearly identical positions where they could interact with the $Mg^{2+}$ ion. Compound 12 and compound 14 adopt a similar orientation (not shown).

Of the four Gα$_i$ selective-inhibitors disclosed by Appleton et al. (FIG. 1A), compound 12 is the most synthetically tractable. Autodock Vina was used to obtain structure-based information about compound 12. The docked poses of compound 12 were analyzed at the active site of Gα$_i$1-GDP (PDB: 2OM2). It was observed that compound 12 adopted a low energy conformation in which its thiophene-hydoxyl group is inserted in a hydrophobic pocket although it may engage in H-bond interaction with a nearby hydroxyl group of Thr48 that is ideally oriented to H-bond with its imine moiety (FIG. 1Bi). However, this placement of the thiophene-hydoxyl group in the hydrophobic pocket may be counterproductive to the binding affinity of compound 12 as it forces the benzothiophene sulfur group to be oriented in a pocket guarded by hydrophilic residues.

It was postulated that analogs of compound 12 having the thiophene-hydoxyl group deleted or replaced by a small non-polar group could create enhanced binding affinity to Gα$_i$. The phenolic moiety of compound 12 engages in productive interaction with the active site residues. This moiety interacts with the Mg$^{2+}$ bound to GDP (FIG. 1Bii). This may be the key interaction which stabilizes Gα$_i$1-GDP, thereby preventing the exchange of GDP for GTP necessary for activation of Gα$_i$. This observation suggests that modifications at the phenolic moiety of compound 12 may not be well tolerated.

Figure 2:
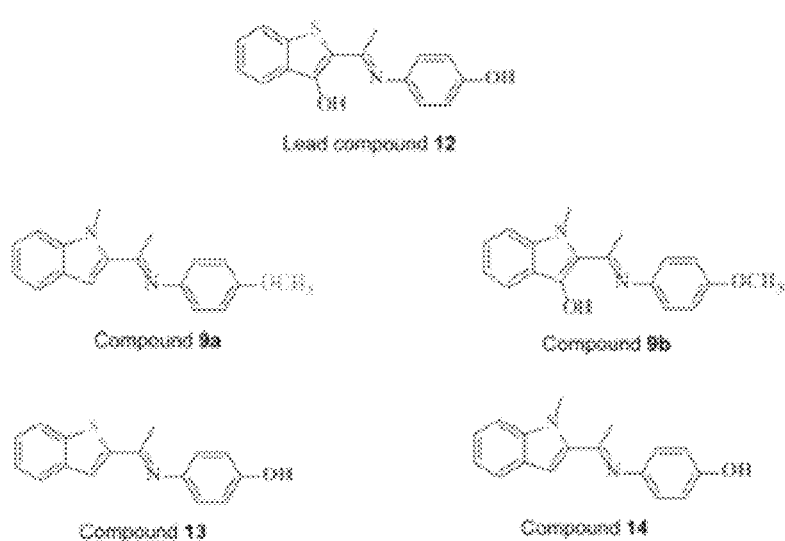
FIG. 2 depicts the structures of $G\alpha_i$ inhibitor compound 12 and the structures of $G\alpha_i2$ inhibitor compounds 9a, 9b, 13 and 14.

To test these inferences, compounds 9a, 9b, 13 and 14 were synthesized (FIG. 2). Compound 13 lacks the thiophene OH-group; compound 14 has a thiol- to N-methyl amino-group substitution. Compounds 9a and 9b are derivatives of 14 designed to test the effect of modification to the phenolic group on Gα$_i$2 inhibition activity. Analysis of the docked outputs of these compounds after molecular docking revealed interesting observations which corroborate several inferences. For example, the methyl ether group in compounds 9a and 9b essentially eliminates the possibility of productive contact with the active site Mg$^{2+}$, possibly depriving the interaction which stabilizes Gα$_i$1-GDP (FIG. 1C).

Compounds 13 and 14 adopt low energy docked orientations with their phenolic groups occupying positions that are nearly identical to that occupied by the phenolic group of compound 12 (FIG. 1Di). The deletion of the thiophene-hydoxyl group in compound 13 forces its benzothiophene to adopt an orientation where its sulfur group is now placed in the hydrophobic pocket occupied by the thiophene-hydoxyl group of compound 12. Also, the N-methyl amino-group of the benzopyrrole moiety of compound 14 is similarly oriented as the benzothiophene sulfur of compound 13 and presumably fits better into the hydrophobic pocket (FIG. 1Dii). Based on these docking results, compounds 13 and 14 are expected to have enhanced Gα$_i$ inhibition activities compared to compound 12 while compounds 9a and 9b are expected to be considerably weaker.

To verify these in silico predictions, compound 12 and compounds 9a-b, 13 and 14 were synthesized following the reaction routes shown in FIG. S1. Compounds 9a and 9b, and 10-11 were synthesized from the corresponding methylketones 1-4 and anisidine (6) or O-silyl-protected p-hydroxyaniline (5 and 7) using catalytic amount of p-TsOH and toluene as solvent. The reactions were performed in Dean-Stark apparatus to remove water, resulting in the target compounds in low to moderate yields. Subsequently, CsF-mediated deprotection of the silyl protection groups of intermediates 8, 10 and 11 furnished the requisite compounds 12, 13 and 14. The compounds were then screened in assays to determine their effect on the intracellular Gα$_i$2 activity and migration of selected cancer cell lines.

Inhibition of Gα$_i$2 Activation Decreases the Migration and Invasion in PC3 Prostate Cancer Cells Endogenous Gα$_i$2 has been found to be essential for cell migration and invasion in prostate cancer cells, in response to different stimuli, such as EGF, oxytocin, TGFβ1 and SDF-1α. To determine the physiological effects of the newly synthesized small molecules, transwell migration assays in PC3 cells were performed using the small molecule inhibitors at three different concentrations (10, 50 and 100 μM). Compound 12, at concentrations of 50 μM and 100 μM, caused a reduction in the migratory capability of PC3 cells, both in the presence and absence of EGF stimulus. At 10 μM, compound 12 had no effect on the migration of the cells (FIG. S2A). Compounds 9a and 9b slightly decreased the migratory capability of PC3 cells at 100 μM, but did not affect the EGF-induced cell migration at the concentrations of 10 and 50 μM (FIGS. S2B and S2C). At concentrations of 10, 50 and 100 μM, compounds 13 and 14 reduced the migratory capability of PC3 cells in presence of EGF, compared with the control cells (FIGS. S2D-S2E).

Cell viability assays for all the tested compounds were performed at 10, 50 and 100 μM concentrations. Compounds 12, 13 and 14 were found to be cytotoxic at 50 and 100 μM, but had no effect on cell viability at 10 μM. Compounds 9a and 9b had no effect on cell viability.

Based on these results, compounds 13 and 14 were used at 10 μM concentrations in all further experiments and compound 9b was used as a negative control.

At 10 μM, compounds 9b and 12 had no effect on migration of PC3 cells in the presence of EGF. However, compounds 13 and 14 significantly decreased EGF-induced migratory capability (FIG. 3A). To determine if the small molecules were also able to inhibit the invasive capability of PC3 cells, invasion assays were performed, using compound 14, one of the most effective compounds. As shown in FIG. 3B, the invasive capability of the cells was significantly reduced in the presence of compound 14 in response to both EGF and FBS. Compounds 9b, 13 and 14 did not affect cell viability at the concentration of 10 μM (FIG. 3C).

The Inhibitor 14 Blocks Activation of Gα$_i$2

To establish the specificity of the newly synthesized compounds against Gα$_i$2, PC3 cells were incubated with compound 14 (10 μM) for 30 minutes and then treated with EGF (10 ng/ml) or OXT (200 nmol/L) for an additional 30 minutes. Immunoprecipitation using anti-active Gα$_i$ antibody was performed and Western blot analysis was conducted using specific anti-Gα$_i$2 antibody. It was observed that, after treatments with OXT, the levels of active Gα$_i$2 were increased, compared to the control; however, EGF treatments did not induce the activation of Gα$_i$2 protein. Moreover, in the presence of compound 14, the levels of active Gα$_i$2 were reduced after stimulation with OXT, compared to the controls. PTX treatments were used as positive controls, which caused significant reduction in the levels of active Gα$_i$2 in both control and OXT-stimulated cells (FIG. 5A).

Subsequently, constitutively active form of Gα$_i$2 (Gα$_i$2-Q205L) was overexpressed in DU145 cells and the effects of the inhibitors on cell migration in these cells were determined. As shown in FIG. 5B, overexpression of Gα$_i$2-

Q205L in DU145 cells led to a significant increase in cell migration that was not further increased in the presence of EGF, compared to the cells transfected with empty vectors (DU145-EV). Treatments with compound 14 (10 μM) resulted in the attenuation of basal and EGF-stimulated cell migration in DU145 cells overexpressing constitutively active Gα$_i$2 (Gα$_i$2-Q205L) (FIG. 5B).

Gα$_i$2 Protein is Essential for Cell Migration in Breast and Ovarian Cancer Cells.

Figures 6A, 6B, 6C, 6D:
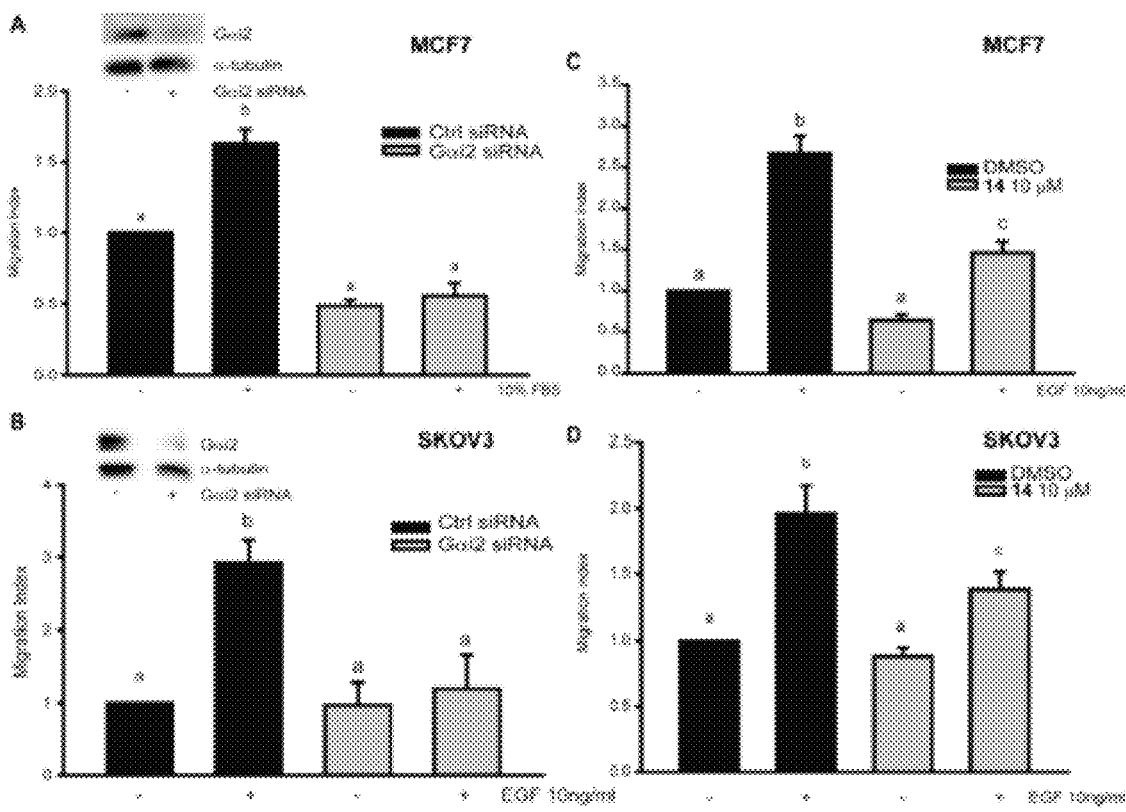
FIG. 6A is a bar graph depicting cell migration assays of MCF7 cells transfected with control and $G\alpha_i2$ siRNAs and then subjected to transwell migration assays in the presence of 10% FBS. Results are expressed as migration index. Each bar represents mean f SEM (n=3). Different letters represents significant differences (P<0.05) among various treatment groups.
FIG. 6B is a bar graph depicting cell migration assays of SKOV3 cells transfected with control and $G\alpha_i2$ siRNAs and then subjected to transwell migration assays in the presence of 10 EGF (10 ng/ml). Results are expressed as migration index. Each bar represents mean±SEM (n=3). Different letters represents significant differences (P<0.05) among various treatment groups.
FIG. 6C is a bar graph depicting cell migration assays of MCF7 cells treated with and without compound 14 at 10 μM and then subjected to transwell migration assays in the presence of 10% FBS. Results are expressed as migration index. Each bar represents mean f SEM (n=3). Different letters represents significant differences (P<0.05) among various treatment groups.
FIG. 6D is a bar graph depicting cell migration assays of SKOV3 cells treated with and without compound 14 at 10 μM and then subjected to transwell migration assays in the presence of 10 EGF (10 ng/ml). Results are expressed as migration index. Each bar represents mean±SEM (n=3). Different letters represents significant differences (P<0.05) among various treatment groups.
Figure 7:
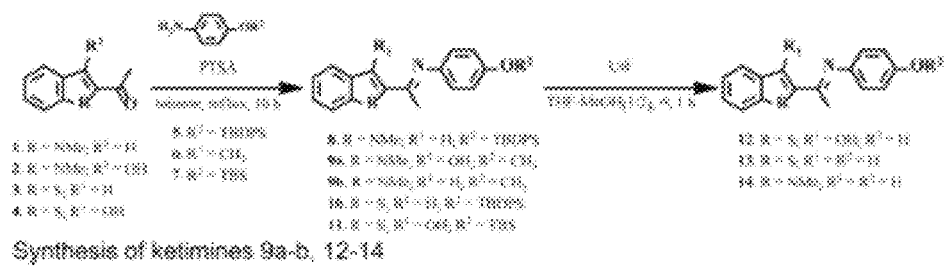
FIG. 7 depicts the reaction routes for the synthesis of compounds 9a, 9b, 12, 13 and 14.
Figures 8A, 8B, 8C, 8D, 8E:
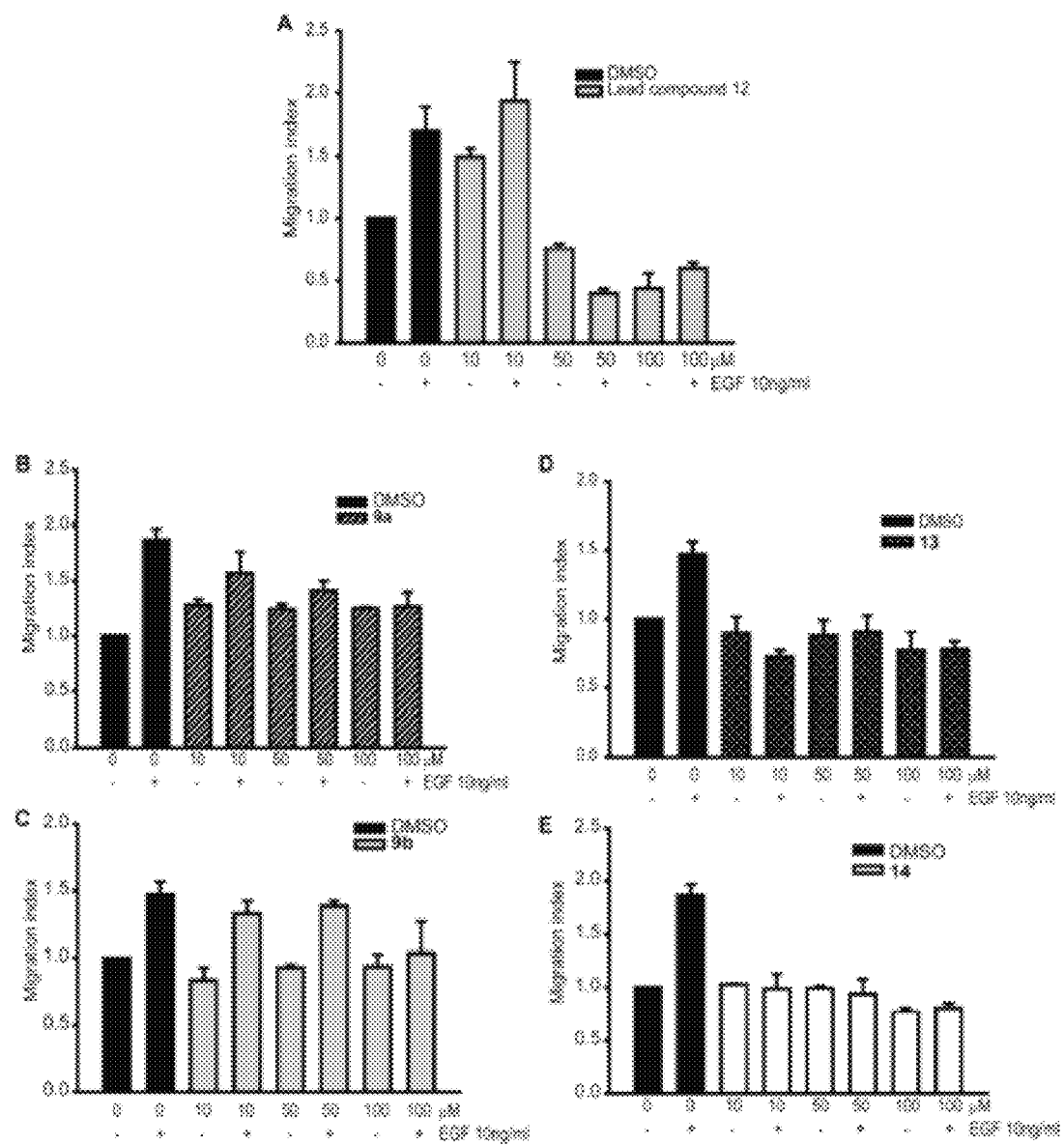
FIG. 8A is a graph depicting migration assays in PC3 cells using compound 12 at concentrations of 10 μM, 50 μM and 100 μM.
FIG. 8B is a graph depicting the migration assays in PC3 cells using compound 9a at concentrations of 10 μM, 50 μM and 100 μM.
FIG. 8C is a graph depicting the migration assays in PC3 cells using compound 9b at concentrations of 10 μM, 50 μM and 100 μM.
FIG. 8D is a graph depicting the migration assays in PC3 cells using compound 13 at concentrations of 10 μM, 50 μM and 100 μM.
FIG. 8E is a graph depicting the migration assays in PC3 cells using compound 14 at concentrations of 10 μM, 50 μM and 100 μM.

The essential role of Gα$_i$2 protein in the migration of prostate cancer cell lines has been shown. To determine whether Gα$_i$2 plays a similar role in other cancers, migration assays using breast and ovarian cancer cell lines were performed. In MCF7 (human breast adenocarcinoma cell lines) and SKOV3 (ovarian cancer cell lines), the knockdown of Gα$_i$2 protein resulted in significant reduction in the number of migrating cells in FBS and EGF treated cells, compared with the cells transfected with control siRNAs (FIG. 6A-B). Treatments with compound 14 (10 μM) also impaired the migratory capability of both cell lines (FIG. 6C-D).

---

We claim:

1. A compound having the following structure:

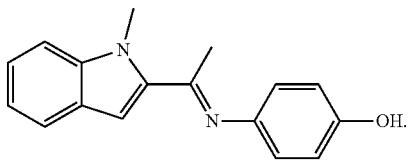 [SMILES: C/C(=N\c1ccc(O)cc1)c1cc2ccccc2n1C]

2. A compound having the following structure:

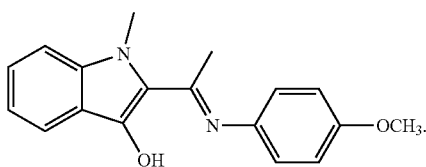 [SMILES: COc1ccc(/N=C(\C)c2c(O)c3ccccc3n2C)cc1]

3. A compound having the following structure:

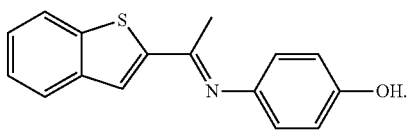 [SMILES: C/C(=N\c1ccc(O)cc1)c1cc2ccccc2s1]

4. A method of treating cancer, comprising administering to a subject in need thereof a compound of Formula I or Formula II:

I wherein, $R^1$, $R^2$ and $R^3$ are each independently selected from the group consisting of H, OH and halogen;

$R^4$ is selected from the group consisting of H, alkyl, halo-alkyl, aryl, and pyridyl, wherein the aryl and pyridyl groups are optionally substituted at the ortho, meta and para positions;

$R^5$ is selected from the group consisting of H, methyl and ethyl;

$R^6$ is selected from the group consisting of H, OH and halogen; and $R^7$ is OH or OMe;

II wherein, $R^{1a}$, $R^{2a}$ and $R^{3a}$ are each independently selected from the group consisting of H, OH and halogen;

$R^{4a}$ is selected from the group consisting of H, alkyl, halo-alkyl, aryl and pyridyl, wherein the phenyl and pyridyl are optionally substituted at the ortho, meta and para positions;

$R^{5a}$ is selected from the group consisting of H, methyl and ethyl;

$R^{6a}$ is H or halogen;

$R^{7a}$ is OH or OMe; and,

X is S or O;

to inhibit cell migration in prostate cancer, breast cancer, or ovarian cancer.

5. A method of treating cancer, comprising administering to a subject in need thereof a compound having the structure:

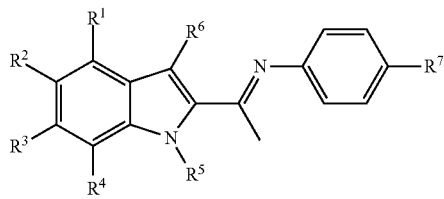

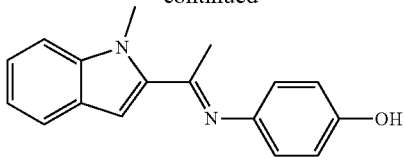

to inhibit cell migration in prostate cancer, breast cancer, or ovarian cancer.

6. The method of claim 4, wherein $R^1$, $R^2$ and $R^3$ each independently selected from the group consisting of H, OH, Cl, Br and I;

$R^4$ is selected from the group consisting of H, methyl, ethyl, trifluoromethyl, phenyl and pyridyl, wherein the phenyl and pyridyl are optionally substituted at the ortho, meta and para positions;

$R^5$ is selected from the group consisting of H, methyl and ethyl;

$R^6$ is selected from the group consisting of H, OH, Cl, Br and I;

$R^{1a}$, $R^{2a}$ and $R^{3a}$ are each independently selected from the group consisting of H, OH, Cl, Br and I;

$R^{4a}$ is selected from the group consisting of H, methyl, ethyl, trifluoromethyl, phenyl and pyridyl, wherein the phenyl and pyridyl are optionally substituted at the ortho, meta and para positions;

$R^{5a}$ is selected from the group consisting of H, methyl and ethyl;

$R^{6a}$ is selected from the group consisting of H, Cl, Br and I;

$R^{7a}$ is OH or OMe; and,

X is S or O.

* * * * *

UNITED STATES PATENT AND TRADEMARK OFFICE
CERTIFICATE OF CORRECTION

PATENT NO. : 12,084,418 B2
APPLICATION NO. : 17/556820
DATED : September 10, 2024
INVENTOR(S) : Khan et al.

Page 1 of 1

It is certified that error appears in the above-identified patent and that said Letters Patent is hereby corrected as shown below:

In the Claims

Column 21,
Line 12, Claim 6, "each" should read --are each--.

Signed and Sealed this
Eighteenth Day of March, 2025

Coke Morgan Stewart
*Acting Director of the United States Patent and Trademark Office*

SEQUENCE LISTING

<160> NUMBER OF SEQ ID NOS: 2

<210> SEQ ID NO 1
<211> LENGTH: 354
<212> TYPE: PRT
<213> ORGANISM: Homo sapiens

<400> SEQUENCE: 1

```
Met Gly Cys Thr Leu Ser Ala Glu Asp Lys Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
            35                  40                  45

Ile Val Lys Gln Met Lys Ile Ile His Glu Ala Gly Tyr Ser Glu Glu
        50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
    130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
    210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Asp Thr Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
        275                 280                 285
```

Glu Tyr Ala Gly Ser Asn Thr Tyr Glu Glu Ala Ala Tyr Ile Gln
            290                 295                 300

Cys Gln Phe Glu Asp Leu Asn Lys Arg Lys Asp Thr Lys Glu Ile Tyr
305                 310                 315                 320

Thr His Phe Thr Cys Ala Thr Asp Thr Lys Asn Val Gln Phe Val Phe
                325                 330                 335

Asp Ala Val Thr Asp Val Ile Ile Lys Asn Asn Leu Lys Asp Cys Gly
                340                 345                 350

Leu Phe

<210> SEQ ID NO 2
<211> LENGTH: 355
<212> TYPE: PRT
<213> ORGANISM: Homo sapiens

<400> SEQUENCE: 2

Met Gly Cys Thr Val Ser Ala Glu Asp Lys Ala Ala Ala Glu Arg Ser
1               5                   10                  15

Lys Met Ile Asp Lys Asn Leu Arg Glu Asp Gly Glu Lys Ala Ala Arg
                20                  25                  30

Glu Val Lys Leu Leu Leu Leu Gly Ala Gly Glu Ser Gly Lys Ser Thr
            35                  40                  45

Ile Val Lys Gln Met Lys Ile Ile His Glu Asp Gly Tyr Ser Glu Glu
        50                  55                  60

Glu Cys Arg Gln Tyr Arg Ala Val Val Tyr Ser Asn Thr Ile Gln Ser
65                  70                  75                  80

Ile Met Ala Ile Val Lys Ala Met Gly Asn Leu Gln Ile Asp Phe Ala
                85                  90                  95

Asp Pro Ser Arg Ala Asp Asp Ala Arg Gln Leu Phe Ala Leu Ser Cys
            100                 105                 110

Thr Ala Glu Glu Gln Gly Val Leu Pro Asp Asp Leu Ser Gly Val Ile
        115                 120                 125

Arg Arg Leu Trp Ala Asp His Gly Val Gln Ala Cys Phe Gly Arg Ser
130                 135                 140

Arg Glu Tyr Gln Leu Asn Asp Ser Ala Ala Tyr Tyr Leu Asn Asp Leu
145                 150                 155                 160

Glu Arg Ile Ala Gln Ser Asp Tyr Ile Pro Thr Gln Gln Asp Val Leu
                165                 170                 175

Arg Thr Arg Val Lys Thr Thr Gly Ile Val Glu Thr His Phe Thr Phe
            180                 185                 190

Lys Asp Leu His Phe Lys Met Phe Asp Val Gly Gly Gln Arg Ser Glu
        195                 200                 205

Arg Lys Lys Trp Ile His Cys Phe Glu Gly Val Thr Ala Ile Ile Phe
210                 215                 220

Cys Val Ala Leu Ser Ala Tyr Asp Leu Val Leu Ala Glu Asp Glu Glu
225                 230                 235                 240

Met Asn Arg Met His Glu Ser Met Lys Leu Phe Asp Ser Ile Cys Asn
                245                 250                 255

Asn Lys Trp Phe Thr Asp Thr Ser Ile Ile Leu Phe Leu Asn Lys Lys
            260                 265                 270

Asp Leu Phe Glu Glu Lys Ile Thr His Ser Pro Leu Thr Ile Cys Phe
        275                 280                 285

Pro Glu Tyr Thr Gly Ala Asn Lys Tyr Asp Glu Ala Ala Ser Tyr Ile
130                 295                 300

```
Gln Ser Lys Phe Glu Asp Leu Asn Lys Arg Lys Asp Thr Lys Glu Ile
305                 310                 315                 320

Tyr Thr His Phe Thr Cys Ala Thr Asp Thr Lys Asn Val Gln Phe Val
                325                 330                 335

Phe Asp Ala Val Thr Asp Val Ile Ile Lys Asn Asn Leu Lys Asp Cys
            340                 345                 350

Gly Leu Phe
        355
```